(12) United States Patent
Kim et al.

(10) Patent No.: US 9,476,038 B2
(45) Date of Patent: *Oct. 25, 2016

(54) ULTRA-HIGH-SPEED NUCLEIC ACID EXTRACTING APPARATUS AND NUCLEIC ACID EXTRACTING METHOD USING SAME

(71) Applicant: NANOBIOSYS INC., Seoul (KR)

(72) Inventors: Sung Woo Kim, Seoul (KR); Duck Joong Kim, Anyang-si (KR); Dong Hoon Lee, Anyang-si (KR); Sun Jin Kim, Seoul (KR); Yong Hea Choi, Seoul (KR); Ho Sun Ryu, Seoul (KR)

(73) Assignee: NANOBIOSYS INC., Seoul (KR)

( * ) Notice: Subject to any disclaimer, the term of this patent is extended or adjusted under 35 U.S.C. 154(b) by 62 days.

This patent is subject to a terminal disclaimer.

(21) Appl. No.: 14/454,388

(22) Filed: Aug. 7, 2014

(65) Prior Publication Data

US 2014/0349386 A1 Nov. 27, 2014

Related U.S. Application Data

(63) Continuation of application No. PCT/KR2013/000609, filed on Jan. 25, 2013.

(30) Foreign Application Priority Data

Feb. 7, 2012 (KR) .................. 10-2012-0012222

(51) Int. Cl.
*C12N 15/10* (2006.01)
*C12Q 1/68* (2006.01)
(Continued)

(52) U.S. Cl.
CPC .......... *C12N 15/1017* (2013.01); *B01L 3/5027* (2013.01); *B01L 2200/10* (2013.01); *B01L 2300/0681* (2013.01); *B01L 2300/0861* (2013.01); *C12M 1/40* (2013.01); *C12Q 1/6806* (2013.01); *C12Q 1/6813* (2013.01); *C12Q 2527/101* (2013.01); *C12Q 2565/629* (2013.01); *G01N 1/34* (2013.01)

(58) Field of Classification Search
CPC .......... C12Q 2565/629; C12Q 1/6806; C12Q 1/6813; C12Q 2527/101; B01L 2200/10; B01L 2300/0681; B01L 2300/0816; B01L 3/5027; C12N 15/1017; G01N 1/34; C12M 1/40

See application file for complete search history.

(56) References Cited

U.S. PATENT DOCUMENTS

2003/0199081 A1* 10/2003 Wilding ............... B01D 61/18
   435/287.2
2006/0205085 A1* 9/2006 Handique ......... B01L 3/502707
   436/177

(Continued)

FOREIGN PATENT DOCUMENTS

CN 101765463 A 6/2010
JP 2009-125033 A 6/2009

(Continued)

*Primary Examiner* — Jennifer Wecker
(74) *Attorney, Agent, or Firm* — Novick, Kim & Lee, PLLC; Sang Ho Lee

(57) ABSTRACT

A nucleic acid extraction device, which can realize automation, ultra-miniaturization and super-high speed in the nucleic acid extraction reaction, has no limitation to the type of biological specimens that can be used, such as sputum, blood, cells, urine, saliva, tissues, etc., minimize the used amount of the sample solution, and also maintain and/or improve the nucleic acid extraction efficiency with reliability.

16 Claims, 4 Drawing Sheets

(51) Int. Cl.
  *B01L 3/00*   (2006.01)
  *C12M 1/40*   (2006.01)
  *G01N 1/34*   (2006.01)

(56) References Cited

U.S. PATENT DOCUMENTS

| | | | |
|---|---|---|---|
| 2007/0048179 A1* | 3/2007 | Fujita | B01L 3/502707 422/400 |
| 2007/0202536 A1* | 8/2007 | Yamanishi | C12Q 1/6881 435/7.1 |
| 2008/0227185 A1* | 9/2008 | Schonfeld | G01N 27/44782 435/287.2 |
| 2008/0257071 A1 | 10/2008 | Wimberger-Friedl et al. | |
| 2010/0021910 A1* | 1/2010 | Cao | C12N 15/1017 435/6.11 |
| 2010/0068706 A1* | 3/2010 | Pourahmadi | G01N 1/34 435/6.19 |
| 2010/0167288 A1* | 7/2010 | Gale | B01L 3/502707 435/6.19 |
| 2010/0216244 A1 | 8/2010 | Wu et al. | |
| 2012/0010097 A1* | 1/2012 | Ohnishi | C12Q 1/6813 506/9 |
| 2012/0053329 A1* | 3/2012 | Yamamoto | C12N 15/1017 530/427 |
| 2013/0302814 A1* | 11/2013 | Haydock | C12Q 1/04 435/6.12 |

FOREIGN PATENT DOCUMENTS

| | | |
|---|---|---|
| JP | 2010-104373 A | 5/2010 |
| JP | 2011-528552 A | 11/2011 |
| JP | 2012-018039 A | 1/2012 |
| KR | 10-0441893 B1 | 7/2004 |
| KR | 10-2009-0124311 A | 12/2009 |
| KR | 10-2011-0035476 A | 4/2011 |
| KR | 10-1082348 B1 | 11/2011 |
| WO | 2008/089493 A2 | 7/2008 |
| WO | 2008/149111 A1 | 12/2008 |
| WO | 2010/009415 A1 | 1/2010 |
| WO | 2010/147654 A2 | 12/2010 |
| WO | 2011/066588 A1 | 6/2011 |

\* cited by examiner

ULTRA-HIGH-SPEED NUCLEIC ACID EXTRACTING APPARATUS AND NUCLEIC ACID EXTRACTING METHOD USING SAME

FIELD OF THE INVENTION

The present invention relates to a device for extracting a nucleic acid from a biological specimen, which includes sputum, blood, cells, urine, saliva, tissues, etc.

BACKGROUND OF THE INVENTION

For diagnosis, treatment, or prevention of diseases at the genetic level, techniques for extracting nucleic acids from a biological specimen such as cells, bacterium, or viruses have recently been in wide use in association with the nucleic acid amplification techniques. The techniques for extracting nucleic acids from the biological specimen are also on demand in various fields of applications, such as customized drug development, forensic, detection of endocrine disruptors, and so forth.

An example of the conventional nucleic acid extraction techniques is a method of solubilizing a specimen including cells with SDS or proteinase K, modifying and removing proteins with phenol, and then purifying a nucleic acid. However, the phenol-based extraction method has a credibility problem because the phenol-based extraction method requires a number of steps, which takes a lot of time, and the efficiency of the nucleic acid extraction method greatly depends on the worker's experience and skills. To resolve this problem, a kit having silica or glass fiber that specifically combines with a nucleic acid has been recently used. The silica or glass fiber has a low combining ratio with proteins or cell metabolites, so it is possible to acquire a nucleic acid at a relatively high concentration. This method is advantageous because it is more convenient in comparison to the phenol-based method. But the method uses a chaotropic reagent or ethanol that strongly inhibits the enzyme reaction such as polymerization chain reaction (PCR) or the like and thus requires a complete removal of the substances, that is, the chaotropic reagent or ethanol, so it could be an onerous task and takes a longer time. Recently, International Publication No. WO 00/21973 discloses a method of directly purifying a nucleic acid with a filter. The method involves passing a specimen through the filter to retain cells adsorbed by the filter, dissolving the adsorbed cells, filtering the cells, and then washing and eluting the adsorbed nucleic acid. However, in order to obtain the nucleic acid after adsorbing the cells with the filter, the method further requires the selection of the filter depending on the type of the cells. Another disadvantage is that the devices used in this method are too large and complicated for the worker to use with ease.

SUMMARY OF THE INVENTION

In view of the aforementioned problems of the conventional nucleic acid extraction techniques, the present disclosure provides a device for extracting a nucleic acid from a biological specimen. The device includes a substrate, a microfluidic chip having an inlet portion, an outlet portion, a channel connecting the inlet portion and the outlet portion, and a filter disposed in the channel and having a porous structure, a chip support disposed on one side of the substrate and including a chip receiving portion defining a space so that the chip receiving portion houses the microfluidic chip therein, and a heater disposed in the substrate and configured to apply heat to a part of the microfluidic chip.

The chip receiving portion may have a shape of a plate with a horizontal surface in close contact with one side of the microfluidic chip.

The heater may be a contact plate type heating block, and transfer the heat to the microfluidic chip by a surface contact.

The device further includes a chip cover being arranged on one side of the chip support and having a horizontal surface in close contact with another side of the microfluidic chip.

The device further includes a fluid control module configured to control the flow of a reactant solution in the microfluidic chip.

The device further includes a heat control unit connected to the heater to control an amount of heat applied to a reactant solution in the microfluidic chip.

The channel may include a first channel region, a second channel region, a third channel region and a fourth channel region.

The filter may include a first filter and a second filter.

The microfluidic chip may further include a heating portion disposed in the first channel region connected to the inlet portion and configured to transfer the heat obtained from an exterior to the biological specimen introduced from the inlet portion, the first filter arranged in the second channel region connected to the heating portion and filtering a substance having a size larger than that of the nucleic acid out, a nucleic acid separating portion arranged in the third channel region connected to the first filter and having a nucleic acid binding substance capable of specifically binding with the nucleic acid, the second filter arranged in the fourth channel region connected to the nucleic acid separating portion and filtering the substance having a size larger than that of the nucleic acid out, and the outlet portion connected to the second filter.

The channel includes the first to the fourth channel regions of the microfluidic chip is configured to allow a fluid to pass through and have a width and a depth in a range of 0.001 to 10 mm, respectively.

The first and second filters of the microfluidic chip may have a pore in a diameter range of 0.1 to 0.4 µm and in a thickness range of 0.01 to 0.5 mm.

The first and second filters of the microfluidic chip may have a pore having a diameter of 0.2 µm and a thickness of 0.01 to 0.5 mm.

The nucleic acid separating portion of the microfluidic chip may have a bead with a nucleic acid binding functional group on the surface thereof as a nucleic acid binding substance.

The bead having a nucleic acid binding functional group of the microfluidic chip for nucleic acid extraction has a diameter in a range of 0.001 to 20 mm.

The nucleic acid separating portion of the microfluidic chip for nucleic acid extraction includes the bead having a nucleic acid binding functional group in an amount of 1 µg to 200 mg.

The microfluidic chip for nucleic acid extraction may be made of a plastic material.

The microfluidic chip includes a first plate, a second plate being arranged on the first plate and having a channel comprising the first to fourth channel regions, and a third plate being arranged on the second plate and having the input portion and the output portion.

The first and third plates of the microfluidic chip for nucleic acid extraction includes a material selected from the group consisting of polydimethylsiloxane (PDMS), cycloolefin copolymer (COC), polymethylmethacrylate (PMMA), polycarbonate (PC), polypropylene carbonate (PPC), polyether sulfone (PES), polyethylene terephthalate (PET), and a mixture of these materials.

The second plate of the microfluidic chip for nucleic acid extraction includes a thermoplastic resin or thermosetting resin material selected from the group consisting of polymethylmethacrylate (PMMA), polycarbonate (PC), cycloolefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoroalkoxyalkane (PFA), and a mixture of these materials.

The inlet portion of the third plate of the microfluidic chip for nucleic acid extraction may have a diameter in a range of 0.1 to 5.0 mm, The outlet portion of the microfluidic chip may have a diameter of 0.1 to 5.0 mm.

The first and third plates of the microfluidic chip may have a thickness in a range of 0.01 to 20 mm respectively.

The second plate of the microfluidic chip may have a thickness in a range of 30 μm to 10 mm.

The device further includes an electronic control unit configured to automatically control the heater, the cover, the fluid control module, and the heat control module wherein the electronic control unit includes a preinstalled software.

According to the nucleic acid extraction device of the present invention, it is possible to realize automation, ultraminiaturization and super-high speed nucleic acid extraction, is not limited to the type of biological specimens that can be used, such as sputum, blood, cells, urine, saliva, tissues, etc., minimizes the used amount of the sample solution, and also maintains and/or improves the nucleic acid extraction efficiency with reliability.

DETAILED DESCRIPTION OF THE PREFERRED EMBODIMENT

Figure 1:
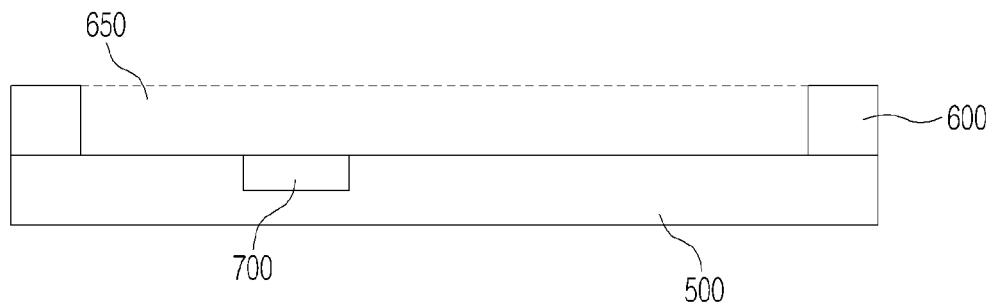
FIG. 1 is a cross section view of a nucleic acid extraction device according to an embodiment of the present disclosure.

Reference will now be made in detail to embodiments, examples of which are illustrated in the accompanying drawings, wherein like reference numerals refer to the like elements throughout the several views. In this regard, the present embodiments may have different forms and should not be construed as being limited to the descriptions set forth herein. Accordingly, the embodiments are merely described below, by referring to the figures, to explain aspects of the present description. Terms used herein are for descriptive purposes only and are not intended to limit the scope of the disclosure. The terms "comprises" and/or "comprising" are used to specify the presence of stated elements, steps, operations, and/or components, but do not preclude the presence or addition of one or more other elements, steps, operations, and/or components. The terms "first," "second," and the like may be used to describe various elements, but do not limit the elements. Such terms are only used to distinguish one element from another. These and/or other aspects become apparent and are more readily appreciated by those of ordinary skill in the art from the following description of embodiments of the present disclosure taken in conjunction with the accompanying drawings. The figures depict embodiments of the present disclosure for purposes of illustration only. The description and specific examples in the disclosure and summary are intended for purposes of illustration only and are not intended to limit the scope of the present invention. One skilled in the art will readily recognize from the following description that alternative embodiments of the structures and methods illustrated herein may be employed without departing from the principles of the disclosure described herein.

FIG. 1 is a cross section view of a nucleic acid extraction device according to an embodiment of the present disclosure. Referring to FIG. 1, the nucleic acid extraction device, according to one embodiment of the present disclosure for extracting a nucleic acid from a biological specimen, includes a substrate 500, a chip support 600 which is arranged on one surface of the substrate 500 and includes a chip receiving portion 650 that has a shape of a plate on a horizontal surface in close contact with one surface of a microfluidic chip for nucleic acid extraction (not shown), and a heater 700 that is designed to apply heat to a part of a bottom surface of the microfluidic chip of the nucleic acid extraction, in which the microfluidic chip is disposed on the chip receiving portion 650.

The nucleic acid extraction device refers to a device designed to perform all the steps for nucleic acid extraction and although not explicitly described herein, may further include various modules required to extract a nucleic acid.

The substrate 500 may be made of any material that does not change physical and/or chemical properties when heated with the heater 700, which is disposed on the substrate 500. The heater 700 will be described further later. Heater 700 maintains the temperature and deformation due to thermal conduction does not occur on the portions other than the heater in the substrate 500. The substrate 500 may be made of, but is not limited to, plastic, glass, silicon, or the like, and the substrate 500 is transparent or semitransparent. The substrate 500 can have various shapes and preferably can be made in the shape of a plate having a horizontal surface as shown in FIG. 1.

The chip support 600 houses and fixes the microfluidic chip for nucleic acid extraction of the present disclosure, which is described in detail later. Thus, the chip support 600 is disposed on one surface of the substrate 500 and can be made of a material that stably houses and fixes the microfluidic chip of nucleic acid extraction (not shown). Furthermore, the chip support 600 has the plate-shaped chip receiving portion 650, which has a horizontal surface that is in close contact with the bottom surface of the microfluidic chip for nucleic acid extraction (not shown). As the chip receiving portion 650 has the shape of a plate, the chip receiving portion 650 makes tight contact with the bottom surface of the microfluidic chip for nucleic acid extraction. This increases the contact area for the heat transfer from the heater 700, which will be described in detail later, and raises the heat transfer rate to enable a stable fluid control of the reactant solution received in the microfluidic chip for nucleic acid extraction so that the nucleic acid extraction reaction can be performed even with a relatively small amount of the reactant solution.

The heater 700 is a module for supplying heat to a part of the microfluidic chip for nucleic acid extraction (not shown) when the microfluidic chip for nucleic acid is mounted on the chip support 600. The heater 700 may be embodied in various manners but preferably may have a contact plate-type heating block in order to increase the heat transfer rate. In one embodiment of the present disclosure, the heater 700 may be disposed on the horizontal surface of the chip receiving portion 650 and is designed to apply heat to a part of the bottom surface of the microfluidic chip for nucleic acid extraction, which is installed in the chip receiving portion 650.

Figure 2:
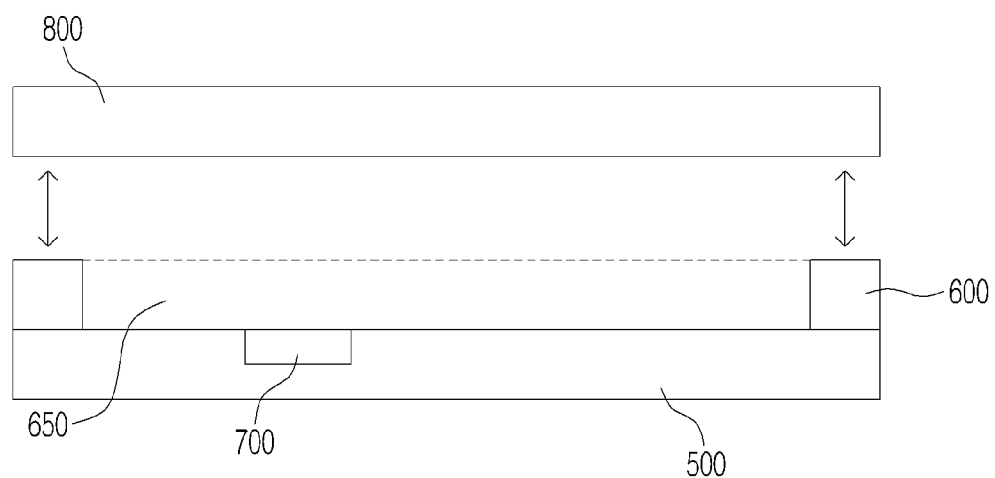
FIG. 2 is a cross section view of the nucleic acid extraction device according to the embodiment of the present disclosure with a chip cover.

FIG. 2 is a cross section view of the nucleic acid extraction device according to the embodiment of the present disclosure with a chip cover.

According to FIG. 2, the nucleic acid extraction device of one embodiment of the present disclosure may further include a chip cover 800 which is disposed on the top of the chip support 600 and has a horizontal surface in close contact with the top surface of the microfluidic chip for nucleic acid extraction (not shown) that is installed in the chip receiving portion 650. The chip cover 800 mounts and stably supports the microfluidic chip used for nucleic acid extraction, and prevents emission of heat from the microfluidic chip, so that the nucleic acid extraction reaction can take place rapidly in the microfluidic chip. The chip cover 800 may have various shapes to achieve the above-described purposes and is preferably made in the shape of a plate.

Figure 3:
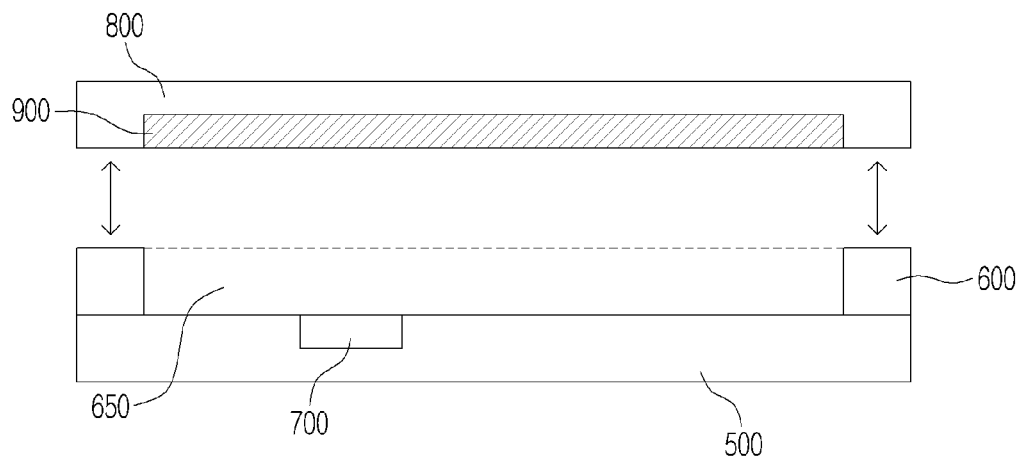
FIG. 3 is a cross section view of the nucleic acid extraction device according to the embodiment of the present disclosure with a fluid control module.

FIG. 3 is a cross section view of the nucleic acid extraction device according to one embodiment of the present disclosure with a fluid control module.

According to FIG. 3, the nucleic acid extraction device according to one embodiment of the present disclosure further includes a fluid control module 900 configured to control the flow of a reactant solution received in the microfluidic chip installed in the chip receiving portion for nucleic acid extraction 650. The fluid control module 900 is connected to the inlet portion (not shown in FIG. 3) and/or the outlet portion (not shown in FIG. 3) of the microfluidic chip installed on the chip support 600 for nucleic acid extraction so that the fluid control module 900 is configured to introduce a solution for nucleic acid extraction into the microfluidic chip for nucleic acid extraction and/or discharge the solution from the inside of the microfluidic chip and/or to control the movement of the reagent solution inside the microfluidic chip. The fluid control module 900 may include various components. For example, the fluid control module 900 may further include a micro-channel as a fluid passage, a pneumatic pump for providing a driving force for fluid flow, a valve for controlling the fluid flow, or a storage chamber containing different solutions required to extract a nucleic acid, such as a nucleic acid binding buffer, an elution buffer, silica gel, distilled water (DW), etc.

Figure 4:
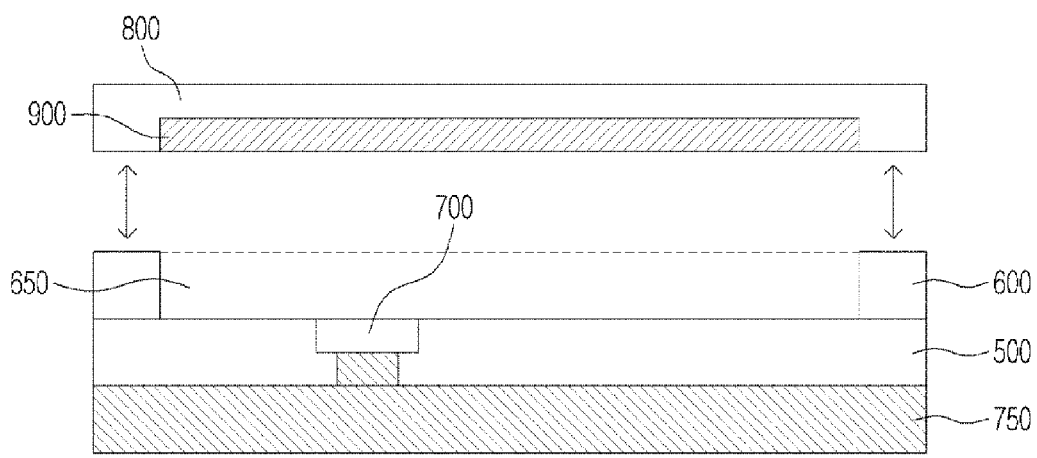
FIG. 4 is a cross section view of the nucleic acid extraction device according to the embodiment of the present disclosure with a heat control module.

FIG. 4 is a cross section view of the nucleic acid extraction device according to one embodiment of the present disclosure with a heat control module.

Referring to FIG. 4, the nucleic acid extraction device according to one embodiment of the present disclosure further includes a heat control module 750 connected to the heater 700 to control the amount of heat provided for a reactant solution accommodated in the microfluidic chip in the chip receiving portion 650 for nucleic acid extraction. By controlling the power supply for the heater 700, the heat control module 750 can control the heating or cooling of the heater 700 so that the nucleic acid extraction reaction can occur according to the temperature and the sequential order as preset in the microfluidic chip for nucleic acid extraction. On the other hand, although not shown in FIG. 4, the nucleic acid extraction device according to one embodiment of the present invention may further include an electronic control module (not shown) to automatically control the heater 700, the cover 800, the fluid control module 900, and the heat control module 750. According to preinstalled software, the electronic control module can precisely control the individual modules to extract a predetermined amount of the nucleic acid in the microfluidic chip for nucleic acid extraction. The preinstalled software includes, for example, a software which is related to and controls a series of steps concerning the nucleic acid extraction.

Figure 5:
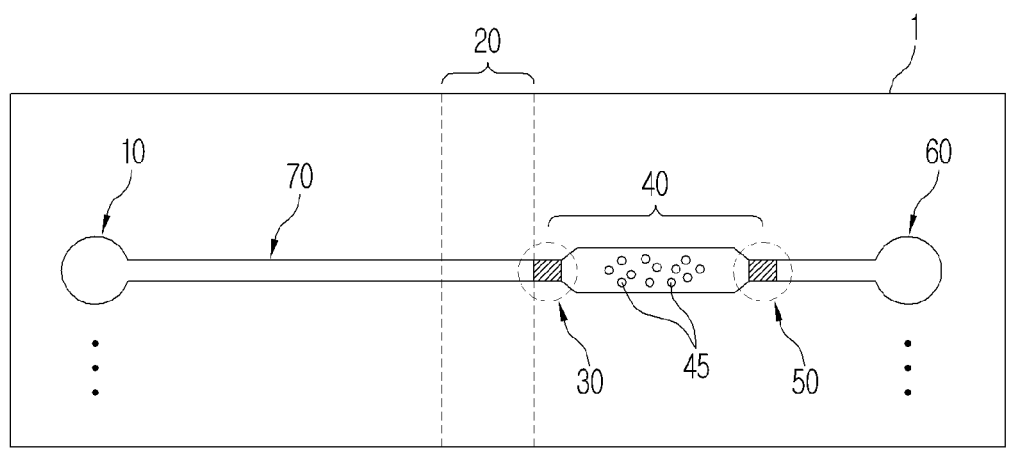
FIG. 5 is a plan view of a microfluidic chip of the nucleic acid extraction device according to the embodiment of the present disclosure.

FIG. 5 is a plan view of the microfluidic chip of nucleic acid extraction device according to one embodiment of the present disclosure.

Referring to FIG. 5, the microfluidic chip 1 for nucleic acid extraction, according to one embodiment of the present disclosure, extracting a nucleic acid from a biological specimen, includes an inlet portion 10, a heating portion 20, a first filter 30, a nucleic acid separating portion 40, a second filter 50, and an outlet portion 60.

The heating portion 20 is disposed in a first channel region that connected to the inlet portion 10. The heating portion 20 is configured to transfer the heat obtained from an exterior to the biological specimen introduced through the inlet portion 10.

The first filter 30 is disposed in a second channel region connected to the heating portion 20. The first filter 30 is configured to pass a substance that has a corresponding size of the nucleic acid.

The nucleic acid separating portion 40 is disposed in a third channel region connected to the first filter 30 and having a nucleic acid binding substance 45 capable of specifically binding with the nucleic acid.

The second filter 50 is disposed in a fourth channel region connected to the nucleic acid separating portion 40. The second filter 50 is configured to pass a substance having a corresponding size of the nucleic acid. The outlet portion 60 is connected to the second filter 50.

The microfluidic chip for nucleic acid extraction as used herein refers to a microchip that includes the components for nucleic acid extraction, such as the inlet portion, the outlet portion, the channel connecting the inlet portion with the outlet portion, the first filter, the second filter, and so forth which are embodied with a size in a millimeter (mm) or micrometer (μm) scale.

The biological specimen as used herein is a biological substance including a nucleic acid such as Deoxyribonucleic acid (DNA) or Ribonucleic acid (RNA). For example, the biological specimen may be a liquid specimen containing but not limited to animal cells, plant cells, pathogenic bacteria, fungi, bacteria, viruses, etc.

The inlet portion 10 is where the biological specimen or the solution for nucleic acid extraction is introduced into the microfluidic chip. The outlet portion 60 discharges the nucleic acid obtained from the biological specimen, the solution for nucleic acid extraction, and/or other wastes from the microfluidic chip. In this case, the inlet portion 10 and the outlet portion 60 may work as an outlet and an inlet, respectively. The solution for nucleic acid extraction includes any solution required for extracting a nucleic acid. Examples of the solution for nucleic acid extraction may include distilled water, a nucleic acid binding buffer, an elution buffer, and so forth. The inlet portion 10 and the outlet portion 60 are connected with each other via a channel 70 so that a fluid can move between them. The components, such as the heating portion 20, the first filter 30, the nucleic acid separating portion 40, and the second filter 50, which will be described in detail later, are disposed in the channel 70 and are configured to perform their respective functions. The channel 70 may be embodied in various sizes, and each of the widths and the depths of the channel 70 are preferably in a range of 0.001 to 10 mm. The terms "first," "second," "third," and "fourth channel regions" are used to merely refer to a sequential order of regions of the microfluidic chip 1 from the inlet portion 10 to the outlet portion 60 and are not used to limit to or indicate specific locations in the channel 70.

The heating portion 20 is where the heat obtained from the exterior is applied to the solution (including the biological specimen) introduced through the inlet portion 10. The heating portion 20 is disposed in the first channel region connected to the inlet portion 10. For example, when a specimen including cells, bacteria, or viruses is introduced through the inlet portion 10, upon arrival at the heating portion 20, the cells, bacteria or viruses is instantly heated to about 80 to 100° C. and their outer cell membranes are destroyed to release the contents of the disrupted cells so that cell lysis can be performed. The heating portion 20 receives the heat via a surface contact from the heater of the nucleic acid extraction device according to one embodiment of the present invention.

The first filter 30 has a porous structure with pores of a predetermined size that filtering out pass-through and non-pass-through substances according to their size in the direction of the fluid. In one embodiment of the present invention, the first filter 30 is arranged in the second channel region connected to the heating portion 20 and designed to allow the substances having an equivalent size of the nucleic acid to pass through. Among the dissolution products resulting from the heating in the heating portion 20, the first filter 30 collects the substances larger than the nucleic acid in the heating portion 20 and allows the nucleic acid and the substances having an equivalent size of the nucleic acid to pass through and move to the nucleic acid separating portion 40 that will be described later. The first filter 30 may be embodied in various sizes, and preferably has pores ranging in size from 0.1 to 0.4 µm in diameter and a thickness ranging from 0.01 to 0.5 mm.

The nucleic acid separating portion 40 is configured to selectively separate the nucleic acid from other substances having an equivalent size of the nucleic acid. Referring to FIG. 5, the nucleic acid separating portion 40 defines a space between the first filter 30 and the second filter 50, which will be described later, and has the nucleic acid binding substance 45 capable of specifically binding with the nucleic acid. The nucleic acid binding substance 45 could be any material that is specifically combined with nucleic acid. The nucleic acid binding substance 45 could be binding beads with a nucleic acid binding functional group and may be, for example, a silica bead or a biotin or streptavidin bead. The bead having a nucleic acid binding functional group may be made in various sizes, but preferably ranging from 0.001 to 20 mm in a diameter. In addition, the nucleic acid separating portion 40 may contain the bead having a nucleic acid binding functional group in different amounts. But, the content of the bead having a nucleic acid binding functional group in the nucleic acid separating portion 40 is preferably in a range from 1 µg to 200 mg. After the nucleic acid is specifically bound to the nucleic acid binding substance 45, the inside of the nucleic acid separating portion 40 is washed to eliminate foreign substances, leaving a complex of the targeted nucleic acid and the nucleic acid binding substance 45 in the nucleic acid separating portion 40. Subsequently, an elution buffer is applied to the nucleic acid separating portion 40 to separate the targeted nucleic acid from the complex.

As described above with respect to the first filter 30, the second filter has a porous structure with pores of a predetermined size that filter out pass-through and non-pass-through substances according to their size. In one embodiment of the present invention, the second filter 50 is arranged in the fourth channel region connected to the nucleic acid separating portion 40 and designed to allow the substances having an equivalent size of the nucleic acid to pass through. The second filter 50 collects the nucleic acid binding substance 45 and passes the nucleic acid separated from the nucleic acid binding substance 45 toward the outlet portion 60. The second filter 50 may be made in various sizes, but preferably with pores ranging from 0.1 to 0.4 µm in diameter and a thickness in a range from 0.01 to 0.5 mm. More preferably, the second filter 50 can have pores having a diameter of 0.2 µm and a thickness of 0.3 mm.

Figure 6:
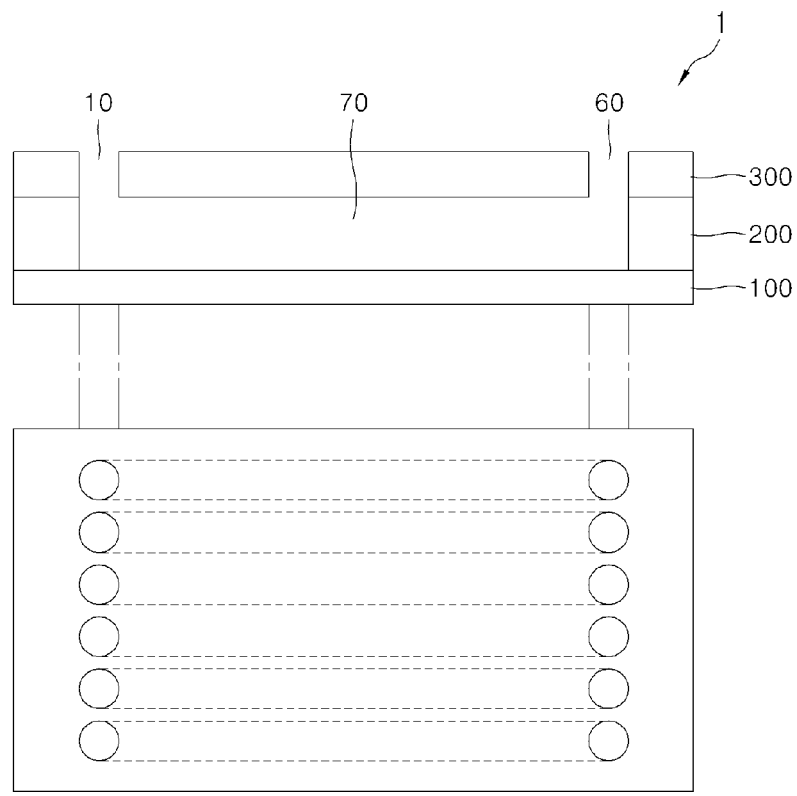
FIG. 6 is a cross section view and a plan view of the microfluidic chip of the nucleic acid extraction device according to the embodiment of the present disclosure.

FIG. 6 is a cross section view and a plan view of the microfluidic chip of the nucleic acid extraction device according to one embodiment of the present disclosure.

According to FIG. 6, the microfluidic chip 1 for nucleic acid extraction according to one embodiment of the present disclosure includes a first plate 100, a second plate 200 which is arranged on the first plate 100 and has a channel 70 including the first to fourth channel regions, and a third plate 300 being arranged on the second plate 200 and having the input portion 10 and the output portion 60. The microfluidic chip 1 for nucleic acid extraction may be formed of different materials but is preferably made of a plastic material. When the microfluidic chip 1 for nucleic acid extraction is made of a plastic material, it is possible to increase the heat transfer efficiency merely by adjusting the thickness of the plastic and to greatly reduce the production cost with the simple production process. On the other hand, the first and third plates 100 and 300 may include a material selected from the group consisting of polydimethylsiloxane (PDMS), cycloolefin copolymer (COC), polymethylmethacrylate (PMMA), polycarbonate (PC), polypropylene carbonate (PPC), polyether sulfone (PES), polyethylene terephthalate (PET), and a mixture of these materials. The second plate 200 may include a thermoplastic resin or thermosetting resin material selected from the group consisting of polymethylmethacrylate (PMMA), polycarbonate (PC), cycloolefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoroalkoxyalkane (PFA), and a mixture of these materials. Further, the inlet portion 10 of the third plate 300 has a diameter in a range of 0.1 to 5.0 mm. The outlet portion 60 of the third plate 300 has a diameter in a range of 0.1 to 5.0 mm. The first and third plates 100 and 300 have a thickness in a range of 0.01 to 20 mm and the second plate has a thickness in a range of 30 μm to 10 mm. In addition, if necessary, the microfluidic chip 1 for nucleic acid extraction according to one embodiment of the present invention may include at least two inlet portions 10 and two outlet portions 20, and channels connecting the portions. In that case, it is possible to extract the nucleic acid from at least two biological specimens on a single chip, thereby achieving extraction of the nucleic acid in a rapid and efficient way.

Figure 7:
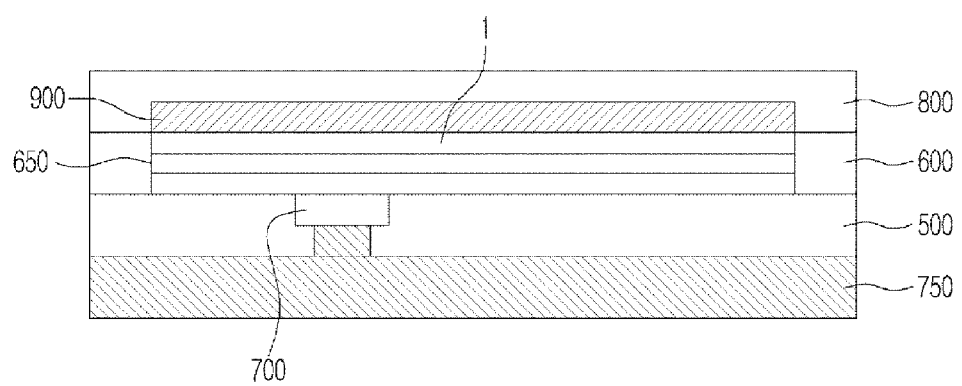
FIG. 7 is a cross section view of the nucleic acid extraction device according to the embodiment of the present disclosure where the microfluidic chip of FIG. 5 is installed therein.

FIG. 7 is a cross section view of the nucleic acid extraction device according to the embodiment of the present disclosure, which the microfluidic chip of FIG. 5 is installed therein.

According to FIG. 7, the nucleic acid extraction reaction can be carried out while the plate-shaped microfluidic chip 1 for nucleic acid extraction is in close contact with the chip receiving portion 650 of the nucleic acid extraction device according to one embodiment of the present invention. More specifically, the method for extracting a nucleic acid from a biological specimen using the nucleic acid extraction device according to one embodiment of the present invention includes a step (microfluidic chip feeding step) of feeding the microfluidic chip 1 for nucleic acid extraction according to one embodiment of the present disclosure, a step (biological specimen introducing step) of introducing a biological specimen, such as sputum, blood, cells, urine, saliva, tissues, etc., through the inlet portion 10 of the microfluidic chip 1, a step (biological specimen lysis step) of transferring the introduced biological specimen to the heating portion 20 of the microfluidic chip 1 and then applying heat to the heating portion 20 of the microfluidic chip 1 through the heater 700 to dissolve the biological specimen; a step (filtration step using the first filter) of transferring the substance obtained from the lysis step to the first filter of the microfluidic chip 1, passing the substance through the first filter and then eliminating the substances that do not pass through the first filter; a step (nucleic acid separation step) of transferring the substances that pass through the first filter to the nucleic acid separating portion of the microfluidic chip 1, binding the nucleic acid among the substances passing through the first filter with the nucleic acid binding substance and then eliminating the substances not binding with the nucleic acid binding substance, a step (filtration step using the second filter) of isolating the nucleic acid from the nucleic acid binding substance, transferring the isolated nucleic acid to the second filter and then passing the nucleic acid through the second filter, and a step (nucleic acid extraction step) of transferring the substances passing through the second filter and then extracting the nucleic acid through the outlet portion. Therefore, the nucleic acid extraction device according to the present invention provides automated, ultra-miniaturized and super-high speed nucleic acid extraction reaction method. According to the present invention, the device can extract nucleic acid from a wide range of biological specimens including: sputum, blood, cells, urine, saliva, tissues, etc. It also minimizes the amount of the sample solution used for testing, and maintains and/or improves the nucleic acid extraction efficiency with reliability.

Experimental Example

Yield of Nucleic Acid Extraction and Required Time

First, a general nucleic acid extraction device using a tube and a nucleic acid extraction device using a microfluidic chip for nucleic acid extraction according to one embodiment of the present invention are independently used to extract DNAs from a cell of the tubercular *bacillus* strain, and the yield of the DNAs and the required time are determined.

The general nucleic acid extraction step is as follows. The cell of the tubercular *bacillus* strain is prepared and mixed with 6% NaOH and 4% N-acetyl-L-cysteine (NALC) at a mixing ratio of 1:1:1 to prepare a sample solution. The sample solution is subjected to a centrifugal separation and the supernatant is removed (20 min, 4,300 rpm, 4° C.). 1 ml of distilled water (DW) is added to the sample solution and, after vortexing, the sample solution is transferred to another tube. The sample solution is subjected to a second centrifugal separation and then the supernatant is removed (3 min, 12,000 rpm, room temp.). 1 ml of distilled water (DW) is added to the sample solution and, after vortexing, 500 μl of distilled water (DW) is added to the sample solution. DNA is obtained using a commercially available QIAamp DNA Kit. As a result, the yield of the final product is about 100 μl and the required time to obtain the final DNA product is at least about one hour.

Subsequently, the microfluidic chip 1 for nucleic acid extraction and the nucleic acid extraction device according to one embodiment of the present invention are used to extract the nucleic acid from the same cell of the tubercular *bacillus* strain. The specific procedures are as follows. The cell of the tubercular *bacillus* strain is prepared and mixed with 6% NaOH and 4% NaLC at a mixing ratio of 1:1:1 to prepare a sample solution. Then, a syringe is used to introduce the sample solution into the inlet portion 10 of the microfluidic chip 1 for nucleic acid extraction (25×72×2 mm³, with trade name SILICA BEADS by OPS Diagnostics, LLC, a filter (Whatman) of FIG. 1 (about one minute required). The first filter 30 can be used, for instance, by PC membrane, with trade name Cyclopore PC Polycarbonate Membranes by Whatman. The second filter 50 can be used, for instance, Nylon net filter, with trade name NY30 by Merck Millipore. Silica gel and 300 μl of a 1×DNA binding buffer are introduced into the inlet portion 10 of the microfluidic chip 1 according to one embodiment of the present invention. And the heating portion 20 of the microfluidic chip 1 according to one embodiment of the present invention is rapidly heated up to 95° C. (about one minute and thirty seconds required). According to one embodiment of the present disclosure, the waste in the sample solution is eliminated and 100 μl of an elution buffer is introduced through the inlet portion 10 of the microfluidic chip 1 (about 30 seconds required). Then, the final product is obtained through the outlet portion of the microfluidic chip according to one embodiment of the present invention. As a result, the yield of the final DNA product is about 100 μl and the required time to obtain the final DNA product is about 7 minutes.

It can be inferred that if the automatic nucleic acid extraction device was used instead of the manual nucleic acid extraction device in the experiment, the required time could be shorten to about 5 minutes or less.

As a result of the experiment, compared to the conventional nucleic acid extraction method, the microfluidic chip and the nucleic acid extraction device according to one embodiment of the present invention can be used to greatly reduce the required time for the nucleic acid extraction while maintaining the yield and amount of the nucleic acid extracted.

It is to be understood that the exemplary embodiments described herein are that for presently preferred embodiments and thus should be considered in a descriptive sense only and not for purposes of limitation. Descriptions of features or aspects within each embodiment should typically be considered as available for other similar features or aspects in other embodiments.

What is claimed is:

1. A device for extracting a nucleic acid from a biological specimen, the device comprising:
a substrate;
a microfluidic chip comprising:
an inlet portion,
an outlet portion, and
a channel connecting the inlet portion and the outlet portion, the channel comprising:
a first channel region extending away from the inlet portion,
a second channel region having a first filter and extended away from the first channel region,
a third channel region having a nucleic acid binding substance and extending away from the second channel region, and
a fourth channel region having a second filter and extended away from the third channel region and connected with the outlet portion;
a chip support disposed on one side of the substrate and including a chip receiving portion housing the microfluidic chip therein; and
a heater disposed in the substrate, the heater being positioned directly adjacent to the first channel region and configured to apply heat to the first channel region, wherein:
the nucleic acid binding substance in the third channel region comprises beads with a nucleic acid binding functional group;
the beads are sandwiched between the first filter and the second filter, each bead of the beads having a diameter in a range of 0.001 to 20 mm;
the first filter and the second filter each comprise a plurality of pores, each pore of the plurality of pores having a diameter range of 0.1 to 0.4 μm; and
the first filter, the second filter, and the beads together form an element of the microfluidic chip configured for nucleic acid extraction.

2. The device as claimed in claim 1, wherein the chip receiving portion has a shape of a plate with a horizontal surface in close contact with one side of the microfluidic chip,
wherein the heater is a contact plate heating block, and
wherein the heater transfers the heat to the microfluidic chip by a surface contact.

3. The device as claimed in claim 1, further comprising:
a chip cover arranged to interpose the microfluidic chip between the chip cover and the chip support and having a horizontal surface in close contact with another side of the microfluidic chip.

4. The device as claimed in claim 1, further comprising:
a fluid control module controlling the flow of a reactant solution in the microfluidic chip.

5. The device as claimed in claim 1, further comprising:
a heat control unit connected to the heater to control an amount of heat in a temperature range from 80° C. to 100° C. and applying the heat to the first channel region.

6. The device as claimed in claim 1,
wherein the microfluidic chip further comprises,
a heating portion disposed in the first channel region transferring the heat obtained from an exterior to the biological specimen introduced from the inlet portion, wherein the heating portion is located adjacent to the second channel region and is disposed to face the heater.

7. The device as claimed in claim 6, wherein the channel including the first to the fourth channel regions of the microfluidic chip allows a fluid to pass through and has a width and a depth in a range of 0.001 to 10 mm.

8. The device as claimed in claim 6, wherein each of the first and second filters of the microfluidic chip has a thickness in a range of 0.01 to 0.5 mm.

9. The device as claimed in claim 8, wherein each of the first and second filters of the microfluidic chip comprises the pore having a diameter of 0.2 μm.

10. The device as claimed in claim 6, wherein the third channel region of the microfluidic chip has the bead with the nucleic acid binding functional group including a silica bead.

11. The device as claimed in claim 10, wherein the third channel region of the microfluidic chip for nucleic acid extraction comprises the bead having a nucleic acid binding functional group in an amount of 1 μg to 200 mg.

12. The device as claimed in claim 6, wherein the microfluidic chip for nucleic acid extraction is made of a plastic material.

13. The device as claimed in claim 6, wherein the microfluidic chip comprises,
a first plate;
a second plate being arranged on the first plate and having a channel comprising the first to fourth channel regions; and
a third plate being arranged on the second plate and having the input portion and the output portion.

14. The device as claimed in claim 13, wherein the first and third plates of the microfluidic chip for nucleic acid extraction comprise a material selected from the group consisting of polydimethylsiloxane (PDMS), cycloolefin copolymer (COC), polymethylmethacrylate (PMMA), polycarbonate (PC), polypropylene carbonate (PPC), polyether sulfone (PES), polyethylene terephthalate (PET), and a mixture of these materials,
wherein the second plate of the microfluidic chip for nucleic acid extraction comprises a thermoplastic resin or thermosetting resin material selected from the group consisting of polymethylmethacrylate (PMMA), polycarbonate (PC), cycloolefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoroalkoxyalkane (PFA), and a mixture of these materials.

15. The device as claimed in claim 13, wherein the inlet portion of the third plate of the microfluidic chip for nucleic acid extraction has a diameter in a range of 0.1 to 5.0 mm,
wherein the outlet portion of the microfluidic chip has a diameter of 0.1 to 5.0 mm,
wherein the first and third plates of the microfluidic chip have a thickness in a range of 0.01 to 20 mm respectively,
wherein the second plate of the microfluidic chip has a thickness in a range of 30 μm to 10 mm.

16. A device for extracting a nucleic acid from a biological specimen, the device comprising:
a substrate;

a microfluidic chip comprising:
  an inlet portion,
  an outlet portion, and
  a channel connecting the inlet portion and the outlet portion, the channel comprising:
    a first channel region extended from the inlet portion,
    a second channel region having a first filter and extended away from the first channel region,
    a third channel region having a nucleic acid binding substance and extending away from the second channel region, and
    a fourth channel region having a second filter and extended away from the third channel region and connected with the outlet portion;
a chip support disposed on one side of the substrate and including a chip receiving portion defining a space housing the microfluidic chip therein; and
a heater disposed in the substrate, the heater being positioned directly adjacent to the first channel region and configured to apply heat to the first channel region;
a heat control unit connected to the heater to control an amount of the heat in a temperature range from 80° C. to 100° C., wherein:

the nucleic acid binding substance in the third channel region comprises beads with a nucleic acid binding functional group;

the beads are sandwiched between the first filter and the second filter, each bead of the beads having a diameter in a range of 0.001 to 20 mm;

the first filter and the second filter each comprise a plurality of pores, each pore of the plurality of pores having a diameter range of 0.1 to 0.4 µm; and the first filter, the second filter, and the beads together form an element of the microfluidic chip configured for nucleic acid extraction.

* * * * *